United States Patent [19]

Waago

[11] Patent Number: 5,006,509

[45] Date of Patent: Apr. 9, 1991

[54] USE OF HUMAN GROWTH HORMONE IN TREATING TOPICAL ULCERS

[76] Inventor: Harald Waago, Breisynvegen 23, N-7021, Trondheim, Norway

[21] Appl. No.: 211,359

[22] Filed: Jun. 24, 1988

[51] Int. Cl.$^5$ .............................................. A61K 37/36
[52] U.S. Cl. ..................................... 514/12; 514/925; 514/928
[58] Field of Search .................... 514/12, 21, 925–928

[56] References Cited

U.S. PATENT DOCUMENTS 4,604,234  8/1986  Fujii ....................................... 514/12

OTHER PUBLICATIONS

Marbindale, The Extra Pharmacopoeia, Twenty Eighth ed., pp. 1661–1662, 1982.
Stedman's Medical Dictionary, 24 ed., Williams and Wilkins, Baltimore, Md., 1982, p. 1509.
The Merck Index, 9th ed., Merck and Co. Inc., Rahway, N.J., 1976, p. 976.

Primary Examiner—F. T. Moezie
Attorney, Agent, or Firm—Darby & Darby

[57] ABSTRACT

A new indication for human growth hormone is described. Mixed with an ointment or other based the growth hormone causes an accelerated healing of ulcers. Described is further a method for the treatment of ulcers comprising applying an effective amount of the growth hormone in an ointment or other base as well as a preparation for use in the above method.

3 Claims, No Drawings

USE OF HUMAN GROWTH HORMONE IN TREATING TOPICAL ULCERS

The present invention is directed to a new use (second indication) of human growth hormone in the treatment of ulcers, a method for treatment of ulcers and a preparation for use in said method.

Until today human growth hormone has, to the Applicant's knowledge, only been used with retarded growth following a decrease of the individual production of the growth hormone (somatotropin).

It is known that in patients who produce too much growth hormone (acromegaly) this hormone causes growth in most of the body's tissues and skin. Since 1963 measurement of the increased growth of soft parts, i.e. skin and skin tissue, has been performed for diagnostic purposes with acromegalic patients. The distance between the heel bone and the footsole is measured. When this distance is greater than 22 mm this gives a strong indication for the diagnosis of acromegaly. A statistical analysis shows that this "heel cushion" normally measures from 13 to 21 mm, with an average of 17.8 mm and a standard deviation of 2 mm. In the acromegalic group of patients the thickness varies from 17 to 34 mm, with an average of 25.8 mm. One has never before tried to utilize this fact in the treatment of ulcers.

It is an object of the present invention to indicate a new use of human growth hormones.

It is another object of the invention to provide a new method for the treatment of ulcers.

It is a further object to provide a preparation to be used in the above-mentioned method.

In the new use of human growth hormone according to the invention the hormone is mixed with an ointment base. Any suitable ointment base may be used together with the human growth hormone, and the invention is in no way limited to the specific example given below.

An ointment base that has been used with great success is cod liver oil in vaselinum; Unguentum Jectoris Aselli, (produced by Norges Apotekerforening (the Association of Norwegian Pharmaceuts)). Cod liver ointment has been produced by Norwegian chemists since before 1940 and belongs to the group of preparations having a strong therapy tradition in the treatment of ulcers and a rather scarce documentation. Medical cod liver oil contains fat, some protein and carbohydrates, besides vitamins A and D. This may be a good nutrient source for growing cells.

The growth hormone that was used in the present investigation was "Nanormon Nordisk" which is available as an injection kit:
1. sterile powder in vials of 4 International Units (IU) growth hormone, amino-acetic acid, sodium bicarbonate and mannitol quant.satis.
2. Ampoule of sterile water 2 ml.

It is marketed under the only indication: retarded growth as a consequence of reduced self production of growth hormone (somatotropin).

The doses of growth hormone used in the present invention will vary from individual depending upon the severity and size of the ulcer, but broadly will range between about 0.5 IU to 20 IU per day, and preferably between 0.5 IU and 1.0 IU. A typical treatment regimen would comprise administration of 1 IU per day divided into two doses, in the morning and late afternoon. Application may also be performed once a day, if desirable.

As a contraindication is cited diabetes mellitus (diabetics). The background for this contraindication is that growth hormone is systemic excess, like various other hormones, is a stress hormone, which enhances the mobilization of sugar stored in the organism. This mechanism increases the level of blood sugar in the serum. Diabetics make extensive use of their own production of stress hormones, including growth hormone, when the blood sugar level becomes too low through use of insulin. In this situation the stress hormones, including the growth hormone, work as a life saver for diabetics. Contraindication, i.e. a rise in the blood sugar level, will therefore depend on the specific situation. For those diabetics who produce too much growth hormone themselves (as in the case of acromegaly) insulin is used to regulate the stipulated rise in blood sugar downwards. In this manner control of the blood sugar level is achieved in patients who themselves produce too much growth hormone. In local ulcer treatment one finds serum levels of growth hormone within normal limits.

Until recently human growth hormone ("Nanormone Nordisk") was produced from necropituitaries from humans. Consequently, the raw materials for the production has been very scarce. For the last couple of years human growth hormone has been produced in the bacterium *Eschericia coli* K12 by use of a recombinant plasmid. The quantity of raw material is therefore no longer a problem. Results with bacterially synthesized human growth hormone appear to be identical to those obtained with growth hormone purified from human pituitaries. (Two preparations of the genetically engineered hormones are as yet registered "Genotropin" from KabiVitrum and "Humantrope" from Eli Lilly.)

The invention will be more fully understood by reference to the following examples which in no way limit the scope of the present invention.

EXAMPLE 1

A 68-year old man with a 36 year history of insulin-dependent diabetes, in whom strict metabolic control had always been difficult, had a history that included an episode of subarachnoid bleeding, progressive retinopathy leading to total blindness, neuropathy with hammer toes and impalpable arteries of the foot. He had had a left below-knee amputation for gangrene at age 64, but walked well with a prosthesis. Two years later he had atrial fibrillation and a cerebral embolism, and in Jan. 1986 two 3×3 cm ulcers developed, one below and one above the right lateral malleolus.

Zinc ointment, antibiotics and wet compresses were tried for 4.5 months. Exfoliatie dermatitis due to penicillin and a right-sided hemiparesis recurred. The hemiparesis subsided as the dermatitis was being treated, but the ulcers were larger. An orthopaedic consultant recommended amputation, but the endocrinologist disagreed.

For another 3 months the ulcers were treated, unsuccessfully, with dressings and "Varidase" ointment (streptokinase) via a window in a walking cast. The largest ulcer then measured 8×5 cm and was 2 cm deep, the ulcer bed with necrotic, and the back of the heel was gangrenous and the naked calcaneum was visible (FIG. 2). Even so amputation was postponed again while, with the patient's consent, local therapy with human growth hormone (GH) was tried.

4 IU of human GH (Nanormone, Nordisk) in sterile powder was mixed with 50 ml of an ointment based on cod liver oil and "Vaseline". The ulcers were monitored every 1-2 weeks for 3 months. The walking cast was retained and dressings were applied twice daily.

From Aug. 25 to Aug. 27 Varidase was given, followed by GH ointment for 6 days. Because of necrosis Varidase was then given for another 6 days. From Sept. 10 to Oct. 8 ointment (4 IU GH in 50 ml) was given and serum levels of GH were below 1.8 mIU/l. On Sept. 27 no necrosis or infection was present. From Oct. 9 to Oct. 17 GH was not available and treatment with ointment base only was not accompanied by an improvement. From Oct. 18 to Nov. 26 ointment with 8 IU GH in 50 ml was given and serum GH concentrations were 5.8 and 6.9 mIU/l. With no further necrosis the large ulcer diminished in size from 4.5×3 cm on Nov. 3 to 3×1.5, 2×1.2 and 1.5×0.6 cm on Nov. 10, 17 and 26, respectively.

Metabolic control was obtained during the last 5 or 6 weeks and the patient was about to be sent home when he was found dead in bed at night. The cause of death was identified as myocardial infarction.

EXAMPLE 2

A 61-year old woman got diabetes mellitus in 1953, 27 years old, and hypertension in 1983, 57 years old. She got nephropathy and went through kidney transplantation in 1985. Thereafter she has used Prednisolon 10 mg. Imurel 75 mg (azathoprin), Sandimmun 200 mg (cyclosporin) per day. These three preparations will slow down ulcer healing.

In 1986 she was diagnosed with retinopathy, neuropathy was also present.

In Feb. 1987 she got an ulcer on the first toe. This was treated in a traditional way for a couple of months. In the first week of May 1987 the joint was visible, and on May 7, amputation was performed. The amputation site looked fine for some days.

Five days after the amputation the wound opened up. The head of the metatarsal bone was visible and had brownish discolored periost. Greyish necrosis covered the ulcer surface. It was possible to move a probe in a pocket 2 cm deep around the whole circumference of the first metatarsal bone. Amputation of the leg was considered, but postponed.

It was then decided to use growth hormone ointment, according to the following schedule:

| | | |
|---|---|---|
| May: | (2 + 2 + 1 + 3) days/per 24 days: | only 8 days with hGH |
| June: | (4 + 7 + 7 + 1) days/per 30 days: | only 19 days with hGH |
| July: | | 31 days with hGH |
| Sum: | | 58 days with hGH |

On Aug. 8th, 1987 the wound had healed.

EXAMPLE 3

A 77 year old woman with hypertension, compensated congestive heart failure got hemiparesis dexter. She was not diabetic. From ultimo Sept. 1987 pressure ulcer developed on the heel.

The ulcer was treated with "Varidase" in Oct. and Nov. 1987 by an orthopaedic surgeon. The ulcer opened up, and late Nov. it measured 4×3.5 cm and the heel bone was uncovered with local grey necrosis. A 2 cm deep pocket appeared under the upper rim of the ulcer.

Amputation was recommended four times by the surgeon, but the patient refused to accept this decision. Foot arteries were not palpable.

From the second week of Dec. 1987 she was treated locally with growth hormone ointment.

After 65 days treatment with growth hormone ointment, the ulcer was healed in Mar. 1988.

The new use of growth hormone and the new method in accordance with the present invention will give a considerably reduced treatment time for patients with chronic ulcers, and consequently considerable economical savings for the health departments.

Many patients with chronic ulcers are today regarded as incurable using conventional methods (as demonstrated in the examples) and amputation is often regarded as the only alternative treatment. The new method for ulcer treatment has also been used with great success with pressure ulcers in elderly non-diabetics.

INDUSTRIAL USES

As the indication for use of the growth hormone has been so limited, its production is not large on a world basis.

In Britain the yearly requirement is calculated to just under 200 new patients per year for the only registered indication: retarded growth through lack of self production of growth hormone. This concerns a population of approx. 60-70 million people. With indication for ulcer treatment it would concern a very large number of patients. For the industry this could mean that production need to increase to a much greater amount. In Norway (population only 4.5 million people) an annual estimate of the number of patients with bed sores is 25,000 patients. Besides this are patients with chronic leg ulcers, burns etc. where a shortened time for treatment would be of great consequence. It could also be of help for skin transplantations to stimulate cell growth.

The target group for this new indication for the use of growth hormone could become very large just in Norway alone.

What is claimed is:

1. A method for treating topical ulcers, in a patient in need of such treatment comprising:
    topically applying to said patient a therapeutically effective amount of human growth hormone in a pharmaceutically acceptable carrier.

2. The method of claim 1, wherein said pharmaceutically acceptable carrier is an ointment.

3. The method of claim 2, wherein said ointment is cod liver oil in petrolatum.

* * * * *